United States Patent [19]

Marzolph et al.

[11] Patent Number: 4,552,890

[45] Date of Patent: Nov. 12, 1985

[54] PLANT PHYTOPATHOGENIC FUNGICIDAL AGENTS BASED ON MALEIMIDE

[75] Inventors: Gerhard Marzolph, Cologne; Heinz U. Blank, Odenthal; Paul Reinecke, Leverkusen; Wilhelm Brandes, Leichlingen; Gerd Hänssler, Leverkusen, all of Fed. Rep. of Germany

[73] Assignee: Bayer Aktiengesellschaft, Leverkusen, Fed. Rep. of Germany

[21] Appl. No.: 578,232

[22] Filed: Feb. 8, 1984

[30] Foreign Application Priority Data

Feb. 26, 1983 [DE] Fed. Rep. of Germany ....... 3306844

[51] Int. Cl.$^4$ .................. A61K 31/40; C07D 207/452
[52] U.S. Cl. .................................... 514/425; 548/548; 548/549
[58] Field of Search ............... 548/549, 548; 424/274; 514/425

[56] References Cited

U.S. PATENT DOCUMENTS

| | | | |
|---|---|---|---|
| 2,962,504 | 11/1960 | Walker et al. | 548/548 |
| 3,129,225 | 4/1964 | Shapiro et al. | 544/141 |
| 3,337,584 | 8/1967 | Knoch | 548/548 |
| 3,364,229 | 1/1968 | Draber et al. | 548/549 |
| 3,734,927 | 5/1973 | Kawada et al. | 548/549 |

FOREIGN PATENT DOCUMENTS

| | | |
|---|---|---|
| 0045907 | 2/1982 | European Pat. Off. . |
| 0098953 | 1/1984 | European Pat. Off. . |
| 880555 | 10/1981 | United Kingdom . |
| 2087879 | 6/1982 | United Kingdom . |

OTHER PUBLICATIONS

Organic Syntheses, vol. 41, 1961, p. 93.

Primary Examiner—Richard L. Raymond
Assistant Examiner—D. B. Springer
Attorney, Agent, or Firm—Sprung Horn Kramer & Woods

[57] ABSTRACT

A method of combatting fungi which comprises applying to fungi or a fungus habitat a fungicidally effective amount of at least one maleic acid N-aralkyl-imide of the formula

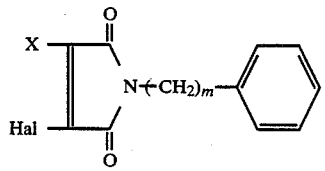

in which
  X is hydrogen or halogen,
  Hal is halogen, and
  m is 2,3 or 4.

Those compounds are new in which
  Hal is chlorine or bromine, and
  X is hydrogen or bromine if m is 2, or
  X is chlorine if m is 4.

12 Claims, No Drawings

PLANT PHYTOPATHOGENIC FUNGICIDAL AGENTS BASED ON MALEIMIDE

The invention relates to the use of maleimide derivatives, some of which are known, as fungicides.

It is already known that halogen-substituted N-aralkyl-maleimides, such as 2,3-dichloromaleic acid N-(2-phenethyl)-imide can be used as compounds having an antibacterial and antiparasitic action in the drug sector (compare U.S. Pat. No. 3,129,225). 2,3-Dichloromaleic acid N-(3-phenyl-propyl)-imide is also known as a substance for use in photochemistry (compare N. Boens, J. Polym. Sci., Polym. Chem. Ed 1975, 13 (1), 201–203 (Engl.)).

Maleic acid N-(2-phenethyl)-imide is known as a seed dressing agent (compare Japanese Pat. No. 78-27,336).

It has now been found that the maleic acid N-aralkyl-imides, some of which are known, of the formula (I)

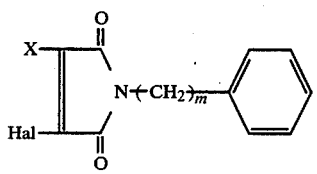

in which
X represents hydrogen or halogen,
Hal represents halogen and
m represents an integer from 2 to 4,
have good fungicidal actions in the field of plant protection.

Surprisingly, the maleic acid N-aralkyl-imides of the formula (I) exhibit a broader and better action against fungi than the compounds known from the prior art.

Formula (I) provides a definition of the compounds which can be used according to the invention. In the formula, preferably,
X represents hydrogen, fluorine, chlorine or bromine,
Hal represents fluorine, chlorine or bromine and
m represents the number 2, 3 or 4.

Particularly preferred compounds of the formula (I) are those in which
X represents hydrogen, chlorine or bromine,
Hal represents chlorine or bromine and
m represents 2, 3 or 4.

Some of the compounds according to the invention are new, but they can be prepared by processes which are known in principle, for example by reacting
(a) a halogenomaleic anhydride of the formula (II)

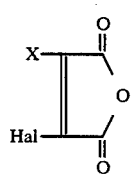

in which
X and Hal have the abovementioned meaning, with primary amines of the formula (III)

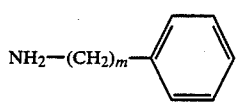

in which
m has the abovementioned meaning, in a diluent, or
(b) a dialkyl halogenomaleate of the formula (IV)

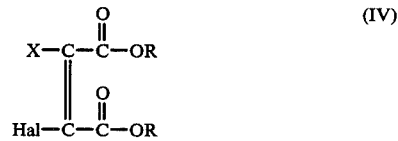

in which
X and Hal have the abovementioned meaning and
R represents alkyl, with primary amines of the formula (III) in which
m has the abovementioned meaning, if appropriate in a solvent or diluent, or
(c) by cyclizing halogenomaleic acid monoamides of the formula (V)

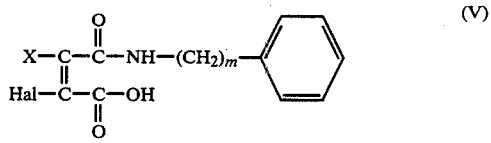

in which
X, Hal and m have the abovementioned meaning, to the compounds of the formula (I) in the presence of a solvent, such as, for example, glacial acetic acid, and if appropriate of (a dehydrating) agent, such as, for example, acetic anhydride or thionyl chloride.

Formula (II) provides a general definition of the halogenomaleic anhydrides required as starting compounds in carrying out process variant (a). These compounds are commercially available and/or can easily be prepared by known processes. Formula (III) provides a definition of the amines also to be used in process variants (a) and (b). The amines are known in some cases, or they can be prepared by generally known processes. Thus, for example, the amines can be prepared by reduction of nitriles or aldoximes with hydrogen (compare Houben-Weyl, Methoden der organischen Chemie [Methods of Organic Chemistry], XI/1, pages 341 et seq.). A current method is also reductive amination of aldehydes with hydrogen and ammonia (compare Houben-Weyl, XI/1, page 341). The method of reduction of ω-nitrostyrenes is also suitable for the preparation of aralkylamines (compare Can. J. Chem. 51 (1973) page 1402).

Formula (IV) describes the dialkyl halogenomaleates also required in process variant (b). These esters are known and can be obtained by current processes from the commercially available halogenomaleic anhydrides by reaction with alcohols.

Halogenomaleic acid monoamides of the formula (V) to be used in process variant (c) are known in some cases, and they can be prepared by processes which are known per se from the corresponding maleic anhydrides by reaction with primary amines (compare Organic Synthesis 41, page 93 (1961)).

Possible diluents for process variant (a) are, above all, carboxylic acids, such as, for example, formic acid, acetic acid and propionic acid.

Possible diluents in process variant (b) are organic solvents. These include, preferably, toluene, xylene, chlorobenzene, perchloroethane, dioxane, glycol dimethyl ether and dimethylformamide.

Diluents which are preferably employed in process variant (c) are: carboxylic acids, such as acetic acid; aromatic hydrocarbons, such as toluene or xylene; halogenohydrocarbons, such as chlorobenzene; and furthermore dioxane, and dehydrating agents which are preferably used are acetic anhydride, phosgene, thionyl chloride, phosphorus oxychloride and phosphorus pentachloride.

The reaction temperatures can be varied within a substantial range in carrying out the different process variants. The reaction is carried out at temperatures of 20° to 150° C., preferably 80° to 120° C., in process variant (a). In process variant (b), the reaction is carried out at temperatures from 50° to 180° C., preferably 80° to 130° C., and in process variant (c) the reaction is carried out at temperatures from 0° to 150° C., preferably from 50° to 120° C.

All three variants are in general carried out under normal pressure.

The starting substances are preferably employed in equimolar amounts in carrying out all the process variants.

According to a preferred embodiment of process variant (a), equimolar amounts of the starting substances are stirred in an organic solvent, for example glacial acetic acid, at elevated temperature for several hours. The mixture is then cooled to room temperature and water is added, whereupon the product already precipitates.

If dibromomaleic anhydride is used as the starting substrate, in a preferred embodiment this is prepared in a solution of dibromomaleic acid in which acetic acid, while stirring, and is further reacted directly with the amine in this solution.

According to a preferred embodiment of process variant (b), the dialkyl halogenomaleate is prepared from the dihalogenomaleic anhydride and methanol and is reacted with the amine after fractional distillation. Working up is effected as described above (compare U.S. Pat. No. 3,734,927, Example 5).

The active compounds which can be used according to the invention exhibit a powerful microbicidal action and can be employed in practice for combating undesired micro-organisms. The active compounds which are to be employed are suitable for use as plant protection agents.

Fungicidal agents in plant protection are employed for combating Plasmodiophoromycetes, Oomycetes, Chytridiomycetes, Zygomycetes, Ascomycetes, Basidiomycetes and Deuteromycetes.

The good toleration, by plants, of the active compounds, at the concentrations required for combating plant diseases, permits treatment of above-ground parts of plants, of vegetative propagation stock and seeds, and of the soil.

As plant protection agents, the active compounds according to the invention can be used with particularly good success for combating Venturia species, for example against the apple scab causative organism (*Venturia inaequalis*), for combating Leptosophaeria species, such as, for example, the brown spot disease of wheat causative organism (*Leptospaeria nodorum*), for combating Oomycetes, such as, for example, the leaf rot of potato and tomato causative organism (*Phytophthora infestans*), for combating rice diseases, such as, for example, *Pyricularia oryzae,* and for combating puccinia species, for example against the brown rust of wheat causative organism (*Puccinia recondita*).

The fungicidal action against *Cochliobulus sativus* and *Pyrenophora teres* on cereal as well as the action against organisms causing diseases of seedlings (such as *Rhizoctania solani*) on various cultivated plants, such as cotton and legumes should also be mentioned. In appropriate concentrations, the compounds also have an acaricidal action.

The active compounds can be converted to the customary formulations, such as solutions, emulsions, suspensions, powders, foams, pastes, granules, aerosols, natural and synthetic materials impregnated with active compound, very fine capsules in polymeric substances and in coating compositions for seed, and formulations used with burning equipment, such as fumigating cartridges, fumigating cans, fumigating coils and the like, as well as ULV cold mist and warm mist formulations.

These formulations are produced in known manner, for example by mixing the active compounds with extenders, that is, liquid solvents, liquefied gases under pressure, and/or solid carriers, optionally with the use of surface-active agents, that is, emulsifying agents and/or dispersing agents, and/or foam-forming agents. In the case of the use of water as an extender, organic solvents can, for example, also be used as auxiliary solvents. As liquid solvents, there are suitable in the main: aromatics, such as xylene, toluene or alkyl naphthalenes, chlorinated aromatics or chlorinated aliphatic hydrocarbons, such as chlorobenzenes, chloroethylenes or methylene chloride, aliphatic hydrocarbons, such as cyclohexane or paraffins, for example mineral oil fractions, alcohols, such as butanol or glycol as well as their ethers and esters, ketones, such as acetone, methyl ethyl ketone, methyl isobutylketone or cyclohexanone, strongly polar solvents, such as dimethylformamide and dimethylsulphoxide, as well as water; by liquefied gaseous extenders or carriers are meant liquids which are gaseous at normal temperature and under normal pressure, for example aerosol propellants such as halogenated hydrocarbons as well as butane, propane, nitrogen and carbon dioxide; as solid carriers there are suitable: for example ground natural minerals, such as kaolins, clays, talc, chalk, quartz, attapulgite, montmorillonite or diatomaceous earth, and ground synthetic minerals, such as highly-dispersed silicic acid, alumina and silicates; as solid carriers for granules there are suitable: for example crushed and fractionated natural rocks such as calcite, marble, pumice, sepiolite and dolomite, as well as synthetic granules of inorganic and organic meals, and granules of organic material such as sawdust, coconut shells, corn cobs and tobacco stalks; as emulsifying and/or foam-forming agents there are suitable: for example non-ionic and acid anionic emulsifiers, such as polyoxyethylene-fatty acid esters, polyoxyethylene-fatty alcohol ethers, for example alkylaryl polyglycol ethers, alkyl sulphonates, alkyl sulphates, aryl sulphonates as well as albumin hydrolysis products; as dispersing agents there are suitable: for example lignin-sulphite waste liquors and methylcellulose.

Adhesives such as carboxymethylcellulose and natural and synthetic polymers in the form of powders, granules or latices, such as gum arabic, polyvinyl alcohol and polyvinyl acetate, can be used in the formulations.

It is possible to use colorants such as inorganic pigments, for example iron oxide, titanium oxide and Prussian Blue, and organic dyestuffs, such as alizarin dyestuffs, azo dyestuffs and metal phthalocyanine dyestuffs, and trace nutrients such as salts of iron, manganese, boron, copper, cobalt, molybdenum and zinc.

The formulations in general contain between 0.1 and 95% by weight of active compound, preferably between 0.5 and 90%.

The active compounds according to the invention can be present in the formulations or in the various use forms as a mixture with other known active compounds, such as fungicides, bactericides, insecticides, acaricides, nematicides, herbicides, bird repellents, growth factors, plant nutrients and agents for improving soil structure.

The active compounds can be used as such or in the form of their formulations or the use forms prepared therefrom by further dilution, such as ready-to-use solutions, emulsions, suspensions, powders, pastes and granules. They are used in the customary manner, for example by watering, immersion, spraying, atomizing, misting, vaporizing, injecting, forming a slurry, brushing on, dusting, scattering, dry dressing, moist dressing, wet dressing, slurry dressing or encrusting.

In the treatment of parts of plants, the active compound concentrations in the use forms can be varied within a substantial range. They are, in general, between 1 and 0.0001% by weight, preferably between 0.5 and 0.001%.

In the treatment of seed, amounts of active compound of 0.001 to 50 g per kilogram of seed, preferably 0.01 to 10 g are generally required.

For the treatment of soil, active compound concentrations of 0.00001 to 0.1% by weight, preferably 0.0001 to 0.02%, are required at the place of action.

USE EXAMPLES

The compounds shown below are used as the comparison substance in the examples which follow:

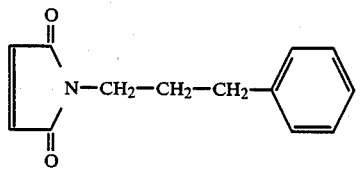
(A)

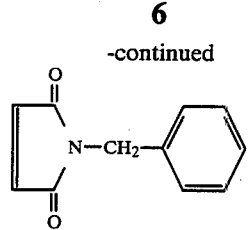
(B)

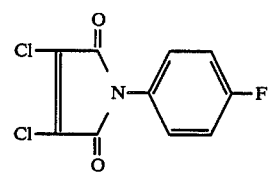
(C)

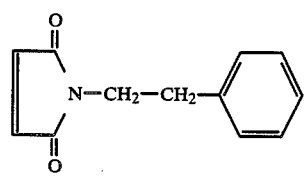
(D)

EXAMPLE A

Puccinia test (wheat)/protective
Solvent: 100 parts by weight of dimethylformamide
Emulsifier: 0.25 parts by weight of alkylaryl polyglycol ether To produce a suitable preparation of active compound, 1 part by weight of active compound is mixed with the stated amounts of solvent and emulsifier, and the concentrate is diluted with water to the desired concentration.

To test for protective activity, yound plants are inoculated with a spore suspension of *Puccinia recondita* in a 0.1% strength aqueous agar solution. After the spore suspension has dried on, the plants are sprayed with the preparation of active compound until dew-moist. The plants remain in an incubation cabin at 20° C. and 100% relative atmospheric humidity for 24 hours.

The plants are placed in a greenhouse at a temperature of about 20° C. and a relative atmospheric humidity of about 80% in order to promote the development of rust pustules.

Evaluation is carried out 10 days after the inoculation.

In this test, a clearly superior activity compared with the prior art is shown, for example by the compounds according to the following preparation examples 2, 4, 5, 1 and 3, as shown in Table A:

TABLE A

| Puccinia test (wheat)/protective | | | |
|---|---|---|---|
| Active compound | | Active compound concentration in the spray liquor in % by weight | Disease infestation in % of the untreated control |
| 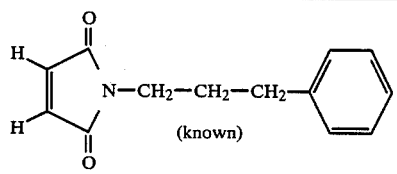 (known) | (A) | 0.025 | 58.7 |

TABLE A-continued

Puccinia test (wheat)/protective

| Active compound | | Active compound concentration in the spray liquor in % by weight | Disease infestation in % of the untreated control |
|---|---|---|---|
| Cl—C(=O)—C(Cl)=C(Cl)—C(=O)—N—CH₂—CH₂—C₆H₅ (maleimide structure) | (2) | 0.025 | 0.0 |
| Cl—C(=O)—C(Cl)=C(Cl)—C(=O)—N—CH₂—CH₂—CH₂—C₆H₅ | (4) | 0.025 | 21.3 |
| Cl—C(=O)—C(Cl)=C(Cl)—C(=O)—N—CH₂—CH₂—CH₂—CH₂—C₆H₅ | (5) | 0.025 | 25.0 |
| H—C(=O)—C(H)=C(Cl)—C(=O)—N—CH₂—CH₂—C₆H₅ | (1) | 0.025 | 25.0 |
| Br—C(=O)—C(Br)=C(Br)—C(=O)—N—CH₂—CH₂—C₆H₅ | (3) | 0.025 | 25.0 |

EXAMPLE B

*Leptosphaeria nodorum* test (wheat)/protective
Solvent: 100 parts by weight of dimethylformamide
Emulsifier: 0.25 parts by weight of alkylaryl polyglycol ether To produce a suitable preparation of active compound, 1 part by weight of active compound is mixed with the stated amounts of solvent and emulsifier, and the concentrate is diluted with water to the desired concentration.

To test for protective activity, young plants are sprayed with the preparation of active compound until dew-moist. After the spray coating has dried on, the plants are sprayed with a conidia suspension of *Leptosphaeria nodorum*. The plants remain for 48 hours in an incubation cabin at 20° C. and 100% relative atmospheric humidity.

The plants are placed in a greenhouse at a temperature of about 15° C. and a relative atmospheric humidity of about 80%.

Evaluation is effected 10 days after the inoculation.

In this test, a clearly superior activity compared with the prior art is shown, for example, by the compounds according to the following preparation examples 2, 4, 1 and 3, as shown in Table B:

TABLE B

*Leptosphaeria nodorum* test (wheat)/protective

| Active compound | | Active compound concentration in the spray liquor in % by weight | Disease infestation in % of the untreated control |
|---|---|---|---|
| Maleimide N-CH2-phenyl (known) | (B) | 0.025 | 100 |
| 2,3-dichloromaleimide N-CH2-CH2-phenyl | (2) | 0.025 | 0.0 |
| 2,3-dichloromaleimide N-CH2-CH2-CH2-phenyl | (4) | 0.025 | 20.0 |
| 3-chloromaleimide N-CH2-CH2-phenyl | (1) | 0.025 | 16.7 |
| 2,3-dibromomaleimide N-CH2-CH2-phenyl | (3) | 0.025 | 25.0 |

EXAMPLE C

Phytophthora test (tomato)/protective
Solvent: 4.7 parts by weight of acetone
Emulsifier: 0.3 parts by weight of alkylaryl polyglycol ether To produce a suitable preparation of active compound, 1 part by weight of active compound is mixed with the stated amounts of solvent and emulsifier, and the concentrate is diluted with water to the desired concentration.

To test for protective activity, young plants are sprayed with the preparation of active compound until dripping wet. After the spray coating has dried on, the plants are inoculated with an aqueous spore suspension of *Phytophthora infestans*.

The plants are placed in an incubation cabin at 100% relative atmospheric humidity and at about 20° C.

Evaluation is carried out 3 days after the inoculation.

In this test, a clearly superior activity compared with the prior art is shown, for example, by the compounds according to the invention, as follows:

TABLE C

Phytophthora test (tomato)/protective systemic

| Active compound | | Infestation in % at an active compound concentration of 250 ppm |
|---|---|---|
| Maleimide N-CH2-CH2-phenyl (known) | (D) | 100 |
| 2,3-dichloromaleimide N-CH2-CH2-phenyl | | 12 |

TABLE C-continued

Phytophthora test (tomato)/protective systemic

| Active compound | Infestation in % at an active compound concentration of 250 ppm |
|---|---|
| 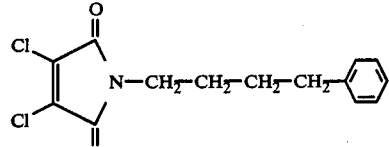 | 50 |

EXAMPLE D

Venturia test (apple)/protective
Solvent: 4.7 parts by weight of acetone
Emulsifier: 0.3 parts by weight of alkylaryl polyglycol ether To produce a suitable preparation of active compound, 1 part by weight of active compound is mixed with the stated amounts of solvent and emulsifier, and the concentrate is diluted with water to the desired concentration.

To test for protective activity, young plants are sprayed with the preparation of active compound until dripping wet. After the spray coating has dried on, the plants are inoculated with an aqueous conidia suspension of the apple scab causative organism (*Venturia inaequalis*) and then remain in an incubation cabin at 20° C. and 100% relative atmospheric humidity for 1 day.

The plants are then placed in a greenhouse at 20° C. and a relative atmospheric humidity of about 70%.

Evaluation is carried out 12 days after the inoculation.

In this test, a clearly superior activity compared with the prior art is shown, for example, by the compounds according to the invention, as follows:

TABLE D

Venturia test (apple)/protective

| Active compound | Infestation in % at an active compound concentration of 250 ppm |
|---|---|
| 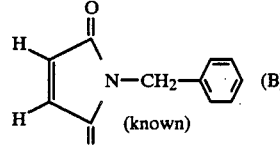 (B) (known) | 60 |

TABLE D-continued

Venturia test (apple)/protective

| Active compound | Infestation in % at an active compound concentration of 250 ppm |
|---|---|
| 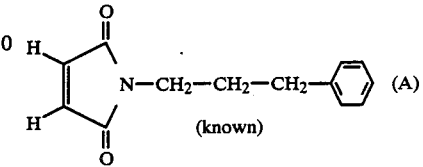 (A) (known) | 68 |
| 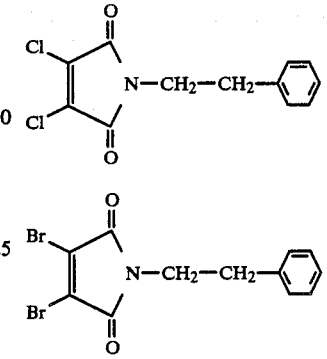 | 37 |
| 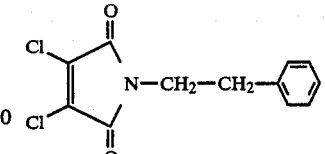 | 10 |

EXAMPLE E

Pyricularia test (rice)/protective
Solvent: 12.5 parts by weight of acetone
Emulsifier: 0.3 parts by weight of alkylaryl polyglycol ether To produce a suitable preparation of active compound, 1 part by weight of active compound is mixed with the stated amount of solvent, and the concentrate is diluted with water and the stated amount of emulsifier, to the desired concentration.

To test for protective activity, young rice plants are sprayed with the preparation of active compound until dripping wet. After the spray coating has dried off, the plants are inoculated with an aqueous spore suspension of *Pyricularia oryzae*. The plants are then placed in a greenhouse at 100% relative atmospheric humidity and 25° C.

Evaluation of the disease infestation is carried out 4 days after the inoculation.

In this test, a clearly superior activity compared with the prior art is shown, for example, by the compounds according to the preparation Example 1, as shown in the following table:

TABLE E

Pyricularia test (rice)/protective

| Active compounds | Active compound concentration in % | Disease infestation in % of the untreated control |
|---|---|---|
| 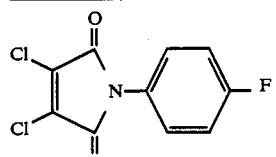 (C) (known) | 0.025 | 100 |

TABLE E-continued

Pyricularia test (rice)/protective

| Active compounds | | Active compound concentration in % | Disease infestation in % of the untreated control |
| --- | --- | --- | --- |
| 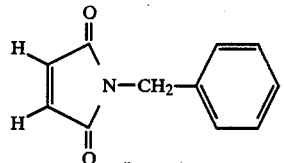 (known) | (B) | 0.025 | 100 |
| 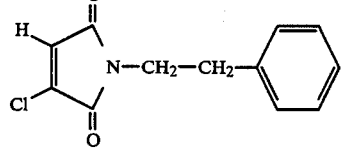 | (1) | 0.025 | 20 |

PREPARATION EXAMPLE

Example 1

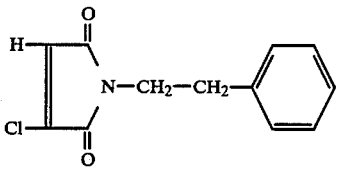

26.5 g (0.2 mol) of chloromaleic anhydride are dissolved in 100 ml of glacial acetic acid. 24.2 g (0.2 mol) of 1-amino-2-phenylethane are then added dropwise and the reaction mixture is subsequently stirred at 100° C. for 4 hours, cooled and stirred with 200 ml of water. The precipitate is filtered off with suction and recrystallized from 150 ml of ethanol. 26.4 g of chloromaleic acid N-(2-phenethyl)-imide (56% of theory) of melting point 119° C. are obtained.

The following compounds of the formula (I)

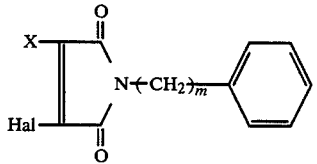 (I)

can be prepared analogously:

| Example No. | X | Hal | m | Melting point (°C.) |
| --- | --- | --- | --- | --- |
| 2 | Cl | Cl | 2 | 131–134 |
| 3 | Br | Br | 2 | 168–169 |
| 4 | Cl | Cl | 3 | 50–51 |
| 5 | Cl | Cl | 4 | 70–71 |

It is understood that the specification and examples are illustrative but not limitative of the present invention and that other embodiments within the spirit and scope of the invention will suggest themselves to those skilled in the art.

We claim:

1. A method of combatting plant pathogenic fungi which comprises applying to such fungi, to a plant, plant part, to seed or to soil a fungicidally effective amount of at least one maleic acid N-aralkyl-imide of the formula

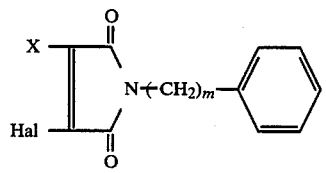

in which
 X is hydrogen or halogen,
 Hal is halogen, and
 m is 2, 3 or 4.

2. A method according to claim 1, in which
 X is hydrogen, fluorine, chlorine or bromine, and
 Hal is fluorine, chlorine or bromine.

3. A method according to claim 1, in which
 X is hydrogen, chlorine or bromine, and
 Hal is chlorine or bromine.

4. The method according to claim 1, wherein such imide is chloromaleic acid N-(2-phenethyl)-imide of the formula

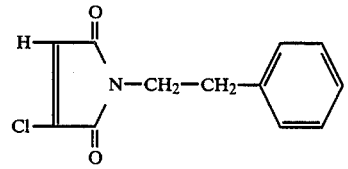

5. The method according to claim 1, wherein such imide is 2,3-dichloromaleic acid N-(2-phenethyl)-imide of the formula

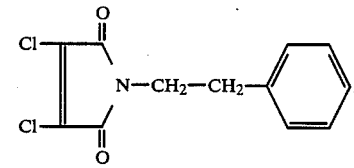

6. The method according to claim 1, wherein such imide is 2,3-dibromomaleic acid N-(2-phenethyl)-imide of the formula

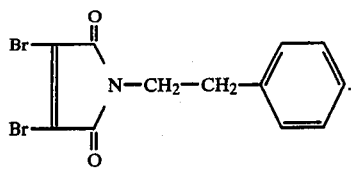

7. The method according to claim , wherein such imide is 2,3-dichloromaleic acid N-(3-phenylpropyl)-imide of the formula

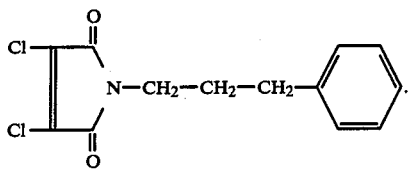

8. A halomaleic acid N-aralkyl-imide selected from the group consisting of
chloromaleic acid N-(2-phenethyl)-imide,
2,3-dibromomaleic acid N-(2-phenethyl)-imide and
2,3-dichloromaleic acid N-(4-phenylbutyl)-imide.

9. A compound according to claim 8, in which said compound is chloromaleic acid N-(2-phenethyl)-imide of the formula

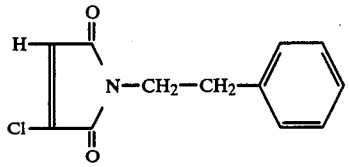

10. A compound according to claim 8, in which said compound is 2,3-dibromomaleic acid N-(2-phenethyl)-imide of the formula

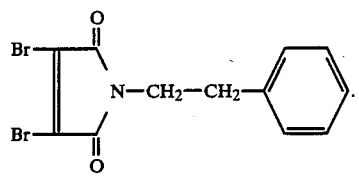

11. A compound according to claim 8, in which said compound is 2,3-dichloromaleic acid N-(4-phenylbutyl)-imide of the formula

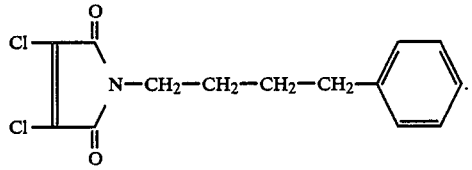

12. A fungicidal composition comprising a fungicidally effective amount of a compound according to claim 8 and a diluent.

* * * * *